(12) United States Patent
Zolentroff et al.

(10) Patent No.: US 6,581,648 B1
(45) Date of Patent: Jun. 24, 2003

(54) METHOD AND APPARATUS FOR OPERATING A SYRINGE AND VIAL FOR INJECTIONS

(75) Inventors: William Carleton Zolentroff, Seattle, WA (US); Robert L. Bode, Bainbridge Island, WA (US); Robert C. Luciano, Park Ridge, IL (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/830,791

(22) PCT Filed: Oct. 8, 1999

(86) PCT No.: PCT/US99/23594
§ 371 (c)(1),
(2), (4) Date: Sep. 14, 2001

(87) PCT Pub. No.: WO00/25846
PCT Pub. Date: May 11, 2000

Related U.S. Application Data

(60) Provisional application No. 60/106,435, filed on Oct. 30, 1998.

(51) Int. Cl.[7] ................................................. B65B 1/04
(52) U.S. Cl. ............................ 141/2; 141/27; 141/329; 604/414
(58) Field of Search .................................. 604/414; 141/2, 141/18, 25–27, 94, 98, 329, 330

(56) References Cited

U.S. PATENT DOCUMENTS

| | | | |
|---|---|---|---|
| 3,853,158 A | 12/1974 | Whitty | 141/27 |
| 4,252,159 A | 2/1981 | Maki | 141/27 |
| 5,115,816 A | 5/1992 | Lee | 128/749 |
| 5,697,916 A | 12/1997 | Schraga | 604/201 |
| 5,716,345 A | 2/1998 | Halbich | 604/207 |

FOREIGN PATENT DOCUMENTS

NL 8006319 11/1980

OTHER PUBLICATIONS

DEBIOJECT "Lyophilized Product Reconstitution" (brochure) (No date).

*Primary Examiner*—Steven O. Douglas
(74) *Attorney, Agent, or Firm*—Drinker Biddle & Reath LLP

(57) ABSTRACT

A device for aligning a vial and a syringe used for medical injections. The device includes a vial alignment portion and a syringe alignment portion, both aligned on an alignment axis extending between the two portions. The alignment portions can restrict motion of both the vial and the syringe transverse to the alignment axis so as to maintain a needle of the syringe aligned with an access port of the vial. The device can also include provisions for removing a protective cap from the vial and for removing a protective cover from the syringe needle. The syring and the vial can be packaged in a container which can also be used to align the syringe with the vial.

34 Claims, 11 Drawing Sheets

METHOD AND APPARATUS FOR OPERATING A SYRINGE AND VIAL FOR INJECTIONS

This application claims the benefit of Provisional application Ser. No. 60/106,435, filed Oct. 30, 1998.

TECHNICAL FIELD

The present invention relates to methods and devices for operating a syringes and vials used for injections of liquid medications.

BACKGROUND OF THE INVENTION

Patients sometimes require injections of liquid medication for treatment of medical conditions. In some cases, it may be inconvenient for the patients to travel to their doctor's offices for each injection and accordingly, the patients and their doctors may prefer to have the patients self-administer their injections.

Arthritis is one condition that can now be treated with periodic injections. In one form, the arthritis medication can include a dry powder in a vial and a liquid diluent in a separate syringe. The patient injects the diluent into the vial, mixes the diluent with the powdered medication to reconstitute the medication, extracts the reconstituted medication into the same syringe, and injects the medication into his or her body with the syringe.

One problem with self-administering arthritis medication is that the patient's dexterity may be severely limited by the arthritic condition. Accordingly, many of the operations necessary to accomplish a self-injection become difficult. Such operations include removing a cover from the needle of the syringe, removing a cap from the vial, aligning the needle of the syringe with the top of the vial, piercing the vial with the needle, and holding the body of the syringe while moving a plunger back and forth within the syringe to first inject the diluent into the vial and then extract the reconstituted medication. Patients with limited dexterity attempting the above operations may not only have difficulty performing the operations, but may also inadvertently contact the needle of the syringe with a non-sanitary surface, and may infect themselves when they subsequently administer the injection. Furthermore, patients may inadvertently stick themselves with the needle prior to administering the injection.

One approach to addressing some of the foregoing problems has been to use an apparatus 2, such as is shown in FIG. 1, to axially align the syringe with the vial. The apparatus 2 includes a vial retainer 4 into which the patient snaps a vial 6, and a shallow syringe cradle 8 into which the patient places a syringe 10 either by sliding the syringe along the groove forming the syringe cradle in a longitudinal direction or by moving the syringe laterally into the syringe cradle in a transverse direction to the main axis of the syringe cradle. The patient slides the syringe 10 along the syringe cradle 8 toward the vial 6, piercing the vial 6 with a needle 11 of the syringe 10. The patient then slides a plunger 12 within the syringe 10 to first inject a diluent into the vial 6 and then withdraw the reconstituted medication from the vial 6. The device 2 also includes a magnifying base 14 to help the patient read the graduations on the syringe 10.

The device 2 shown in FIG. 1 suffers from several drawbacks. For example, the syringe cradle 8 does not limit the lateral motion of the syringe 10 in the transverse direction away from the syringe cradle 8. Accordingly, the patient may not achieve proper axial alignment of the syringe 10 with the vial 6. In addition, the device 2 is sized to properly align only vials and syringes having particular dimensions (for example, particular diameters), and may not accurately align vials and syringes with different dimensions. Furthermore, by not properly aligning the syringe 10 with the vial 6, the user may inadvertently contact the needle 11 with the apparatus 2, thereby contaminating the needle 11. Still further, the apparatus 2 does not address the patient's difficulty in removing a protective needle cover (not shown) from the syringe 10, removing a protective cap (not shown) from the vial 6, or holding the body of the syringe 10 steady in the syringe cradle 8 while moving the plunger 12 within the syringe 10.

SUMMARY OF THE INVENTION

The present invention is directed toward a device for aligning a syringe with a vial. In one embodiment, the device can include a body having a vial alignment portion and a syringe alignment portion, both aligned on an alignment axis extending between the two portions. The vial alignment portion can have at least one vial engagement surface shaped to removably engage the vial, and the syringe alignment portion can have at least one syringe engagement surface shaped to removably engage the syringe. The syringe engagement surface can include a first portion adjacent the syringe and a second portion adjacent the syringe and extending around a portion of the syringe sufficient to at least restrict lateral motion of the syringe in any direction transverse to the alignment axis.

In one aspect of this embodiment, the vial alignment portion and/or the syringe alignment portion can include spaced-apart arms having concave surfaces and being biased toward each other to clamp the vial and/or the syringe therebetween. In a further aspect of this embodiment, the first portion of the syringe engagement surface can be concave, face upwardly, and can extend axially beyond the second portion so as to receive the syringe when the syringe is moved downwardly toward the syringe engagement surface.

In another embodiment, the alignment device can include provisions for removing a cap from the vial and/or removing a needle cover from the syringe. For example, the device can include a cap receiving surface for receiving the cap and an overhanging surface which allows the cap to be pried away from the vial. The device can also include spaced-apart cover engaging surfaces for clamping the needle cover and removing the needle cover from the syringe. In still further embodiments of the invention, the syringe can include a handle and/or a plunger, each having concave engaging surfaces to more readily engage a user's fingers. In yet another embodiment of the invention, the vial alignment portion and syringe alignment portion can be positioned on the surface of a package or container that holds the vial and the syringe within a shipping box during shipping and storage prior to use of the syringe.

The present invention is also directed toward a method for operating a syringe and a vial. In one embodiment, the method includes securing the vial by releasably engaging the vial with an alignment body to at least restrict motion of the vial transverse to an alignment axis extending between the vial and the syringe. The method can further include releasably securing the syringe by engaging the syringe with the alignment body to at least restrict motion of the syringe in all directions transverse to the alignment axis so as to align a needle of the syringe with an access port of the vial.

In one embodiment, the method can further include removing a protective needle cover from the syringe by pressing the needle cover against a grasping member such as a sharpened edge of the alignment body and moving one or the other of the sharpened edge and the needle cover relative to the other to disengage the needle cover from the syringe. In another embodiment, the method can include engaging a cap of the vial with the alignment body and prying the cap away from the vial. In still a further embodiment of the invention, the method can include removing the vial and the syringe from a single container, engaging the vial and the syringe with the container, and restricting motion of at least one of the vial and the syringe away from an alignment axis that extends between the vial and the syringe by engaging either the vial or the syringe with the surface of the container.

DETAILED DESCRIPTION OF THE INVENTION

The present invention is directed toward methods and devices for operating a syringe and a vial used for medical injections. The devices can include portions that align the vial with the syringe and that allow a user to easily access elements of both the vial and the syringe. Many specific details of certain embodiments of the invention are set forth in the following description and in FIGS. 2–10H to provide a thorough understanding of such embodiments. One skilled in the art, however, will understand that the present invention may have additional embodiments and that they may be practiced without several of the details described in the following description.

Figure 1:
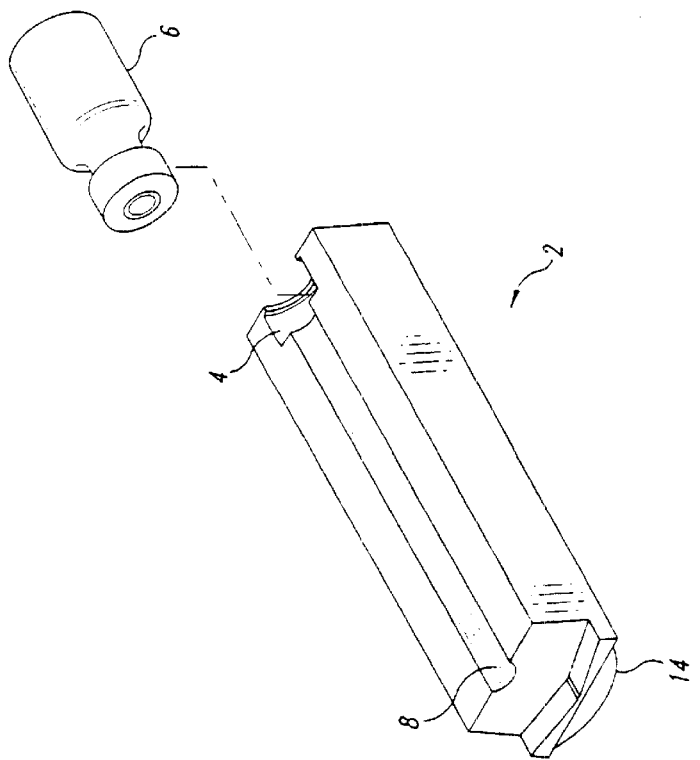
FIG. 1 is a top isometric view of a vial, a syringe and an apparatus in accordance with the prior art.
Figure 1:
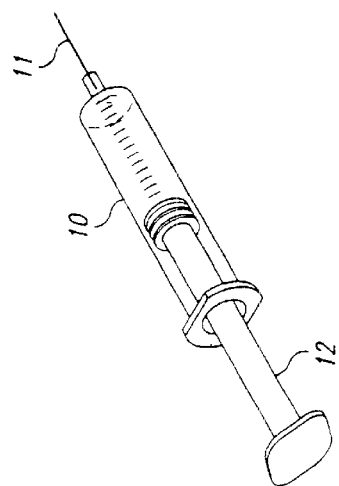
Figure 2:
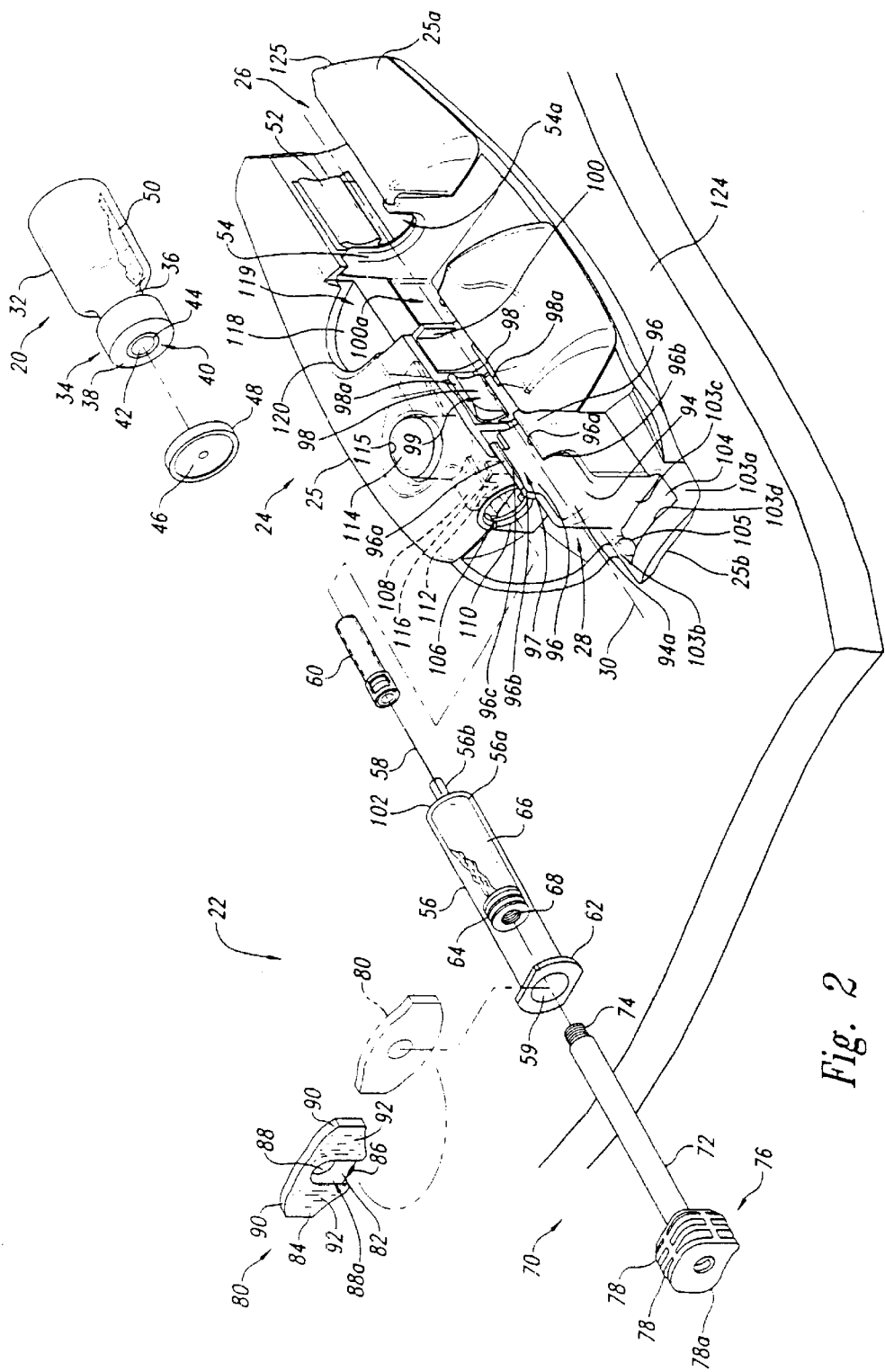
FIG. 2 is a partially exploded top isometric view of a vial, a syringe and an alignment device in accordance with an embodiment of the invention.
Figure 3:
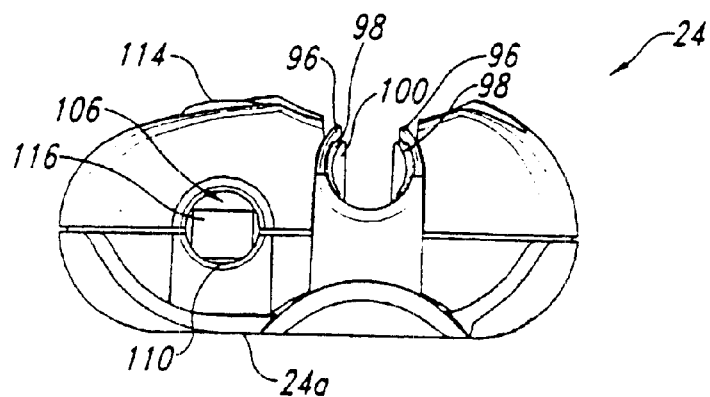
FIG. 3 is a front end view of the device shown in FIG. 2.
Figure 5:
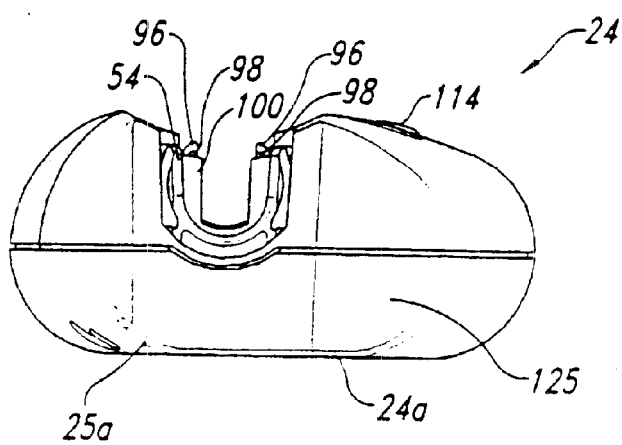
FIG. 5 is a rear end view of the device shown in FIG. 2.

A vial 20, a syringe assembly 22 and an alignment device 24 in accordance with an embodiment of the invention are shown in FIG. 2. The alignment device 24 can include a body 25 having a vial alignment portion 26 toward a rear end 25a and a syringe alignment portion 28 toward an opposite front end 25b. The vial alignment portion 26 and the syringe alignment portion 28 are aligned along an alignment axis 30 that extends along the length of the alignment device 24. The alignment device 24 has a flat bottom surface 24a (best shown in FIG. 6) to provide stability when the alignment device is used resting upon a flat support surface 124 with the vial alignment portion 26 and the syringe alignment portion 28 facing upward as shown in FIG. 2. It is to be understood that the alignment device 24 can be used resting on a surface during at least some of its use or held in the hand during all of its use to prepare the syringe assembly 22 for an injection.

The vial 20 can include a generally cylindrical body 32, a top portion 34 and a neck 36 between the body 32 and the top portion 34. The top portion 34 can include an end surface 38 having an access port 40 that is generally sealed with an elastomeric plug 42. The elastomeric plug 42 has a central target area 44, which is thinner along a longitudinal axis of the body 32 than the rest of the elastomeric plug so as to be easily pierced by the syringe, as will be discussed in greater detail below. The top portion 34 can also include a cap 46 that fits over the end surface 38 to protect the elastomeric plug 42 from contamination and has a cap lip 48 that extends around the edge of the top portion 34. The cap 46 is removed from the vial 20 prior to use, as will also be discussed in greater detail below. In one embodiment, the body 32 of the vial 20 can contain a powdered medication 50 and in other embodiments, the body 32 can contain a liquid medication (not shown).

The vial 20 is removably received and held by the vial alignment portion 26 of the alignment device 24 with a longitudinal axis of the vial in general axial alignment with the alignment axis 30 at the rear end 25a of the body 25 of the alignment device. The vial alignment portion 26 can accordingly include one or more vial engagement surfaces, such as a pair of spaced-apart vial alignment arms 52, one of which is visible in FIG. 2. The vial alignment arms 52 have concave, inwardly facing surfaces that can engage the cylindrical body 32 of the vial 20. In a preferred embodiment, the vial alignment arms 52 are spaced apart at positions on opposite sides of the alignment axis 30 by a distance that is slightly less than the diameter of the body 32, and are resiliently biased toward each other to both center and clamp the vial 20 therebetween on the alignment axis. The vial alignment arms 52 can hold the vial 20 securely in place and permit lateral movement thereof in only one direction (for example, upward as shown in FIG. 2) away from the alignment device 24 and transverse to alignment axis 30 upon application thereby by the user of a predetermined amount of force to move the vial laterally in the one transverse direction. In one aspect of this embodiment, a force of between approximately 10 ounces and approximately 16 ounces in the upward direction can be sufficient to disengage the vial 20 from the vial alignment arms 52. Movement of the vial in other transverse directions is prevented.

In a further preferred aspect of this embodiment, the vial alignment arms 52 can be flexed away from each other (within the confines of the channel-shaped vial alignment portion 26) to accommodate vials 20 having a variety of diameters. Because the vial alignment arms 52 are concave and biased toward each other on opposite sides of the alignment axis 30, they can center a variety of different vials 20 on the alignment axis 30 even if the vials have different diameters. Accurate centering of the vial 20 on the alignment axis 30 can be important because a build-up of manufacturing tolerances in the vial 20, including the dimensions of the plug 42 and the thinner target area 44, may require a fairly precise alignment to hit the target area 44, and if the target area is not hit, it can be impossible to pierce the plug 42 with the needle 58 of the syringe assembly 22.

The vial alignment portion 26 can also include a vial stop wall 54 with a laterally open recess 54a that receives the neck 36 of the vial 20 therein so that the vial stop wall partially encircles the neck 36 when the vial in the vial alignment portion 26 and grasped between the vial alignment arms 52, to restrict axial motion of the vial 20 along the alignment axis 30. The interior diameter of the recess 54a of the vial stop wall 54 is smaller than the diameters of both the body 32 and the top portion 34 of the vial 20, thus the vial stop wall 54 can restrict the vial 20 from movement in either direction along the alignment axis 30. In the embodiment shown in FIG. 2, the axial position of the vial stop wall 54 is fixed and in another embodiment (not shown), the axial position of the vial stop wall 54 can be adjusted to accommodate vials of various lengths. In other embodiments, the vial stop wall 54 or another stop configuration can be sized and shaped to engage any surface of the vial 20 that is inclined relative to the alignment axis 30 to restrict axial motion.

The syringe assembly 22 is removably received and held by the syringe alignment portion 28 of the alignment device 24 with a longitudinal axis of the syringe assembly in general axial alignment with the alignment axis 30 at the front end of the body 25 of the alignment device opposite the vial 20 held by the vial alignment portion 26. The syringe assembly 22 can include a generally cylindrical barrel 56 having a needle 58 at one end and an opening 59 at the opposite end. The needle 58 can be covered with a removable protective needle cover 60 that keeps the needle sterile and prevents accidental needle sticks, and the opening 59 can be encircled with a barrel lip 62, both of which will be discussed in greater detail below. In one embodiment, the barrel 56, needle 58 and needle cover 60 can include a conventional commercially available assembly, such as is available from Becton Dickenson and Company of Franklin Lakes, N.J.

The syringe assembly 22 can also include a piston 64 that sealably engages the inner walls of the barrel 56 and slides axially within the barrel 56. In an embodiment where the vial 20 includes powdered medication 50, the barrel 56 can be pre-loaded with a liquid diluent 66 which is held within the barrel 56 by the piston 64. In another embodiment, where the vial 20 includes a liquid medication, the barrel 56 can be empty or can contain a different liquid.

The piston 64 can also include an internally threaded recess 68 at its end toward the opening 59 for attaching to a plunger 70, which is used to drive the piston 64 axially within the barrel 56. Accordingly, the plunger 70 can include a shaft 72 with a threaded end 74 that can be threadably engaged with the threads of the internally threaded recess 68 of the piston 64 to ready the syringe assembly 22 for use. In one embodiment, the shaft 72 can be hollow for light weight and ease of handling. The shaft 72 can also have a handle portion 76 opposite the threaded end 74. The handle portion 76 can include a plurality of spaced-apart ribs 78 that make the handle portion 76 relatively large so that it can be easily engaged by the user, without making the handle portion 76 unnecessarily heavy, as might be the case with a solid handle. In preferred embodiment, an end face of an outermost rib 78a can be concave or dished-out to receive the convex portion of the user's thumb or other finger (not shown), making it easier for the user to engage the handle portion 76.

The syringe assembly 22 can also include a barrel handle 80 that attaches to the barrel lip 62 to make the barrel 56 easier to manipulate. In one embodiment, the barrel handle 80 can include a front wall 82 and rear wall 84. The barrel handle 80 is shown in FIG. 2 in solid line flipped over to better illustrate the rear wall 84. The front and rear walls 82, 84 are spaced apart from each other so that the barrel handle 80 can receive the barrel lip 62 therebetween. The barrel handle 80 is simply moved laterally to slip over the barrel lip 62 with the plunger 70 removed from the barrel 56. In one embodiment, the front wall 82 can include an inwardly projecting tab 86 that engages a front edge of the barrel lip 62 to hold the barrel handle 80 in place once it is installed on the barrel lip 62.

The front and rear walls 82, 84 of the barrel handle 80 can include an aperture 88 that extends therethrough to allow the plunger 70 to enter the barrel 56 uninhibited by the barrel handle. The aperture 88 in the front wall 82 has a side opening 88a through which the barrel 56 passes when the barrel handle 80 is slipped over the barrel lip 62. The front and rear walls 82, 84 can also extend laterally away from the aperture 88 in opposite directions to form two handle flanges 90. In a preferred embodiment, the rear wall 84 can have concave surfaces 92 in the region of each handle flange 90 to receive the convex portions of the user's fingers. The barrel handle 80 accordingly provides a large, contoured surface area to make holding the barrel 56 easier as the user moves the plunger 70 into and/or out of the barrel 56.

The syringe alignment portion 28, which receives and aligns the syringe assembly 22, can include one or more syringe engagement surfaces, such as an axially extending, base guide surface 94 for receiving thereon and slidably supporting the barrel 56 of the syringe assembly 22 as it is slides therealong to position the syringe assembly in the syringe alignment portion, as will be described in greater detail below, and to support the barrel while allowing minimal lateral movement thereof when positioned in the syringe alignment portion with the needle 58 piercing the elastomeric plug 42. In a preferred embodiment, the base guide surface 94 has an upwardly facing, partially smooth concave shape, as shown in FIG. 2, which has a radius of curvature that corresponds generally to the curvature of the barrel 56 to provide a support surface for the barrel when the barrel is in the syringe alignment portion 28 to reduce movement of the barrel and thereby facilitate obtaining and maintaining alignment of the syringe assembly with the alignment axis 30. The base guide surface 94 is positioned to cradle the barrel 56 with the longitudinal axis of the syringe assembly 22 in general axial alignment with the alignment axis 30. In other embodiments, the base guide surface 94 can have a lengthwise portion thereof with a partially conical shape to help users align the syringe assembly 22 with the alignment axis 30.

The syringe alignment portion 28 can also include two lateral guide surfaces 96 having upper edges 96a that are spaced apart to provide an upwardly open gap 97 through which the needle 58 of the syringe assembly 22 can pass with a lateral movement as an end portion 56a of the barrel 56 of the syringe assembly is lowered onto a front end portion 94a of the base guide surface 94. The lateral guide surfaces 96 have a front end 96b which is positioned rearward of the front end portion 94a of the base guide surface 94 to permit uninhibited downward movement of the end portion 56a of the barrel 56 onto the front end portion 94a. In a preferred embodiment, the lateral guide surfaces 96 are spaced apart at positions on opposite sides of the alignment axis 30 by a distance that is greater than the diameter of the barrel 56 to allow the barrel to pass uninhibited longitudinally therethrough. In addition, the lateral guide surfaces 96 can arch over a sufficient portion of the barrel 56 with the upper edges 96a positioned closely enough together to prevent movement of the barrel 56 therebetween in the transverse direction away from the alignment axis 30. Furthermore, the lateral guide surfaces 96 can include projections 96c that extend inwardly toward the alignment axis 30. In one embodiment, wherein the barrel 56 has a diameter equal to or greater than the spacing between the lateral guide surfaces 96, the lateral guide surfaces 96 can flex relative to the alignment axis and the projections 96c can engage the outer surface of the barrel 56 to provide further alignment of the barrel with the alignment axis.

The syringe alignment portion 28 can also include spaced-apart syringe alignment arms 98. The syringe alignment arms 98 are longitudinally positioned rearward of the lateral guide surfaces 96 along the alignment axis 30. As was discussed above with reference to the vial alignment arms 52, the syringe alignment arms 98 have concave, inwardly facing surfaces that can engage the cylindrical barrel 56 of the syringe assembly 22. The syringe alignment arms 98 are spaced apart at positions on opposite sides of the alignment axis 30 by a distance that is slightly less than the diameter of the barrel 56, and are resiliently biased toward each other to both center and clamp the syringe assembly 22 on the alignment axis 30. The syringe alignment arms 98 hold the barrel 56 securely in place, and can be flexed away from each other (within the confines of the channel-shaped syringe alignment portion 28) to accommodate barrels having a variety of diameters. Because the syringe alignment arms 98 are concave and biased toward each other on opposite sides of the alignment axis 30, they can center a variety of different barrels on the alignment axis 30 even if the barrels have different diameters. The syringe alignment arms 98 have upper edges 98a that are spaced apart to provide an upwardly open gap 99 through which the needle 58 of the syringe assembly 22 can pass with a lateral movement as the end portion 56a of the barrels 56 on the syringe assembly is lowered onto the front end portion 94a of the base guide surface 94. The gap 99 is generally in longitudinal alignment with the gap 97 between the upper edges 96a of the lateral guide surfaces 96.

In one embodiment, the syringe assembly 22 can be removed axially from the alignment device 24 by applying a predetermined axial force to the syringe assembly. For example, when the barrel 56 has a diameter that is smaller than the distance between the lateral guide surfaces 96 but larger than the distance between the syringe alignment arms 98, such that the syringe alignment arms tend to clamp the barrel, a force of between approximately two ounces and approximately three ounces can be sufficient to remove the syringe assembly 22 from the alignment device 24. When the diameter of the barrel is large enough that both the syringe alignment arms 98 and the lateral guide surfaces 96 are flexed away from the barrel while engaging the barrel, a force of between approximately four and approximately five pounds can be sufficient to remove the syringe assembly 22 from the alignment device 24.

The syringe alignment portion 28 can further include a syringe stop wall 100 longitudinally positioned rearward of the syringe alignment arms 98 along the alignment axis 30. The syringe stop wall 100 has a laterally open recess 100a that allows the needle 58 to pass laterally therethrough. The syringe stop wall 100 partially encircles a neck end portion 56b of the barrel 56 from which the needle 58 projects generally coaxial with the barrel and engages an end face 102 of the end portion 56a of the barrel 56 to limit axial movement of the barrel along the alignment axis 30 toward the rear end of the alignment device 24 whereat the vial alignment portion 26 is located. This prevents the barrel 56 from being moved too far toward the vial 20 in the vial alignment portion 26 and the needle 58 from striking the inside bottom surface of the vial. In other embodiments, the syringe stop wall 100 can engage any surface of the syringe assembly 22 that is inclined relative to the alignment axis 30. In still further embodiments, the axial position of the syringe stop wall 100 can be adjustable to accommodate syringes having a variety of needle lengths.

The alignment device 22 can further include a slot 104 adjacent the syringe alignment portion 28 at the front end 25b of the body 25 sized to receive one of the handle flanges 90 of the barrel handle 80 when the barrel handle is rotated such that the handle flanges 90 extend upwardly and downwardly. The slot 104 is defined in part by a pair of laterally spaced apart side wall portions 103a and 103b. The side wall portion 103a is positioned to let the handle flange 90 intended to be positioned in the slot 104 rotate uninhibited thereby and into the slot 104 when the barrel 56 is positioned in the syringe alignment portion 28 with the end face 102 of the barrel against the syringe stop wall 100. The other side wall portion 103b has a handle stop 105 which projects to a position to engage the handle flange 90 rotated into the slot 104 when fully in the slot to prevent the barrel handle 80 from being rotated beyond a selected position. The handle stop 105 is positioned on the side wall portion 103b such that when the plunger 70 is rotated to screw the threaded end 74 thereof into the threaded recess 68 of the piston 64, the barrel handle 80 and hence the barrel 56 are prevented from rotating by the handle stop 105 as a result of the rotational force applied thereto through the piston frictionally engaging the barrel wall. The slot 104 is further defined by a pair of longitudinally spaced-apart end wall portions 103c and 103d. When the barrel handle 80 is rotated into the slot 104 and one of the handle flanges 80 engages the handle stop 105, the end wall portions 103c and 103d hold the one handle flange 90 therebetween and limit axial movement of the barrel 56 in both forward and rearward directions.

The alignment device 22 can also include elements that help the user remove the needle cover 60 from the needle 58 of syringe assembly 22 and remove the cap 48 from the vial 20. For example, the alignment device 22 can include an aperture 106 in the body 25 sized to receive the needle cover 60 therethrough. Inward of the aperture 106, upper and lower needle cover engaging surfaces 108, 110 are positioned to receive and clamp the needle cover 60 therebetween. The user then moves the body 56 of the syringe assembly 22 away from the alignment device 24 to withdraw the needle 58 from the needle cover 60. The needle cover 60 remains in the aperture 106 until removed by the user. In one embodiment, the lower needle cover engaging surface 110 can be a sharpened blade that penetrates or grasps the surface of the needle cover 60 to securely grip the needle cover 60 when the needle cover is pressed to move laterally against the blade. The upper needle cover engaging surface 108 can include a movable concave surface 112 that can be selectively moved toward the needle cover 60 when the needle cover is inserted into the aperture 106 to engage the convex outer surface of the needle cover and thereby move the needle cover firmly against the lower cover engaging surface 110. With the needle cover 60 gripped firmly therebetween, the body 56 of the syringe assembly 22 can be easily moved away from the aperture 106 to expose the needle 58 for passing the needle through the gaps 97 and 99 to position the barrel 56 in the syringe alignment portion 28. The concave surface 112 can be attached to a button 114 which projects upward through an aperture 115 in the body 25 which the user presses downward to clamp the needle cover 60 against the lower needle cover engaging surface 110. The button 114 is biased upward to return to an unclamped position when the user stops pressing the button downward. As shown in FIG. 2 and in FIG. 3, the alignment device 22 can also include a cover stop 116 within the aperture 106 to limit the distance the needle cover 60 is inserted into the aperture 106.

In alternate embodiments (not shown), the needle cover engaging surfaces 108, 110 can have different configurations. For example, in one alternate embodiment, the needle cover engaging surfaces 108, 110 can be connected to each other and can have a generally conical shape that tends to grip the needle cover 60 as the needle cover is advanced into the aperture 106.

The alignment device 24 can include an upward-facing cap receiving surface 118 sized to receive the cap 46 of the vial 20 therein when the cap is attached to the vial. The cap receiving surface 118 is positioned at the base of a recess 119 having a laterally inward open side sized to allow the cap 46 of the vial 20 to pass laterally therethrough to position the cap on the cap receiving surface. An overhang 120 is positioned above and projects over a portion of the perimeter of the cap receiving surface 118. The overhang 120 can be spaced above the cap receiving surface 118 by a sufficient distance to let a rim portion of the cap 46 to be slid under the overhang 120. When the vial 20 is placed face-down with the cap 46 in face-to-face juxtaposition on the cap receiving surface 118, the cap lip 48 can be slid laterally so as to extend beneath the overhang 120. The user can then tilt the vial 20 away from the overhang 120 to pry the cap 46 off the vial 20. The recess 119 is sufficiently large in diameter that the top portion 34 of the vial is uninhibited when the vial 20 is moved upward and out of the recess.

Operation of an embodiment of the alignment device 24 is best understood with reference to FIG. 2. The user may perform the steps of the operation while holding the alignment device 24 in one hand, or while the alignment device 24 rests on the support surface 124.

The user begins operation by removing the cap 48 from the vial 20 using the cap receiving surface 118 and the overhang 120, as discussed above, and swabs the exposed target area 44 of the vial 20 with an alcohol swab (not shown). The user positions the vial 20 along the alignment axis 30 such that the neck 36 is aligned with the recess 54a of the vial stop wall 54 and lowers the vial 20 until the vial alignment arms 52 contact the vial body 32. The user then presses down on the body 32 until the vial alignment arms 52 snap around and grasp the vial body 32. In a preferred embodiment, the body 25 of the alignment device 24 is sized so that if the user inadvertently places the end surface 38 (rather than the neck 36) of the vial 20 adjacent the vial stop wall 54, the vial 20 will project beyond the rear end 25a of the body 25, providing a visual cue that the vial 20 is improperly installed.

The user then prepares the syringe assembly 22 for mounting in the alignment device 24. In one embodiment, the barrel handle 80 will have been previously installed on the barrel 56. In another embodiment, the user slides the barrel handle 80 over the barrel lip 62 until the tab 86 snaps over and engages an edge of the barrel lip 62, securing the barrel handle 80 on the barrel 56. In either case, the user can then align the barrel 56 with the aperture 106 and insert the needle cover 60 into the aperture 106 until the needle cover 60 engages the needle cover stop 116. The user can then press down on the button 114 to clamp the needle cover 60 against the lower needle cover engaging surface 110, and move the barrel 56 away from the alignment device 24, leaving the needle cover 60 clamped between the upper and lower engaging surface 108, 110 and in the aperture 106. When the button 114 is released, the needle cover 60 can fall free of the aperture 106.

In a preferred method of operation, the user next places the alignment device 24 on the flat surface 124. The user can then rotate the barrel 56 until the handle flanges 90 extend to each side relative to the flat surface 124, and can then rest the handle flanges 90 on the surface 124 adjacent the alignment device 24. The user can then move the end portion 56a of the barrel 56 downwardly toward the front end portion 94a of the base guide surface 94 which projects longitudinally forward beyond the front ends 96a of the lateral guide surfaces 96, such that the needle 58 first extends above the gaps 97 and 99 between the lateral guide surfaces 96 and the syringe alignment arms 98. The user then tilts the end portion of the barrel 56 adjacent to the barrel handle 80 upwardly to generally axially align the barrel 56 with the alignment axis 30, and slides the barrel axially to first pass between the lateral guide surfaces 96 and then the syringe alignment arms 98, until the end face 102 of the end portion 56a of the barrel 56 engages the syringe stop wall 100. As this is done, the needle 58 will automatically axially align with the alignment axis 30 and the longitudinal axis of the vial 20 and will pierce the elastomeric plug 42 of the vial. In a preferred embodiment, the syringe assembly 22 is aligned with the vial 20 such that the needle 58 pierces the elastomeric plug 42 and extends only a short distance into the vial so as to increase the amount of liquid that can easily be withdrawn from the vial.

The user then grasps the handle portion 76 of the plunger 70 and inserts the threaded end 74 of the plunger shaft 72 into the barrel 56 and rotates the plunger 70 to engage the threaded end 74 with the threaded recess 68 of the piston 64. As the threaded end 74 is threaded into the piston 64, rotation of the handle portion 76 will eventually cause the barrel handle 80 to rotate into the slot 104 until one of the handle flanges 90 of the handle 80 engages the handle stop 105, thus securing the syringe assembly 22 against further rotation and axial motion. Alternatively, the user can engage the barrel handle 80 directly and rotate it into the slot 104.

Once the barrel handle 80 is received in the slot 104, the user can grasp either the barrel handle 80 or the alignment device 24 and depress the plunger 70 to force the diluent 66 into the vial 20. This can be done while the alignment device 24 is positioned with its flat bottom surface 24a against the flat support surface 124 (as shown in FIG. 2), or while being held in the hand of the user. Alternatively, the alignment device 24 can be positioned with an approximately flat rear surface 125 at the rear end 25a of the body 25 resting on the support surface 124. If the alignment device 24 was being used on the support surface 124, it simply needs to be tipped upward 90° to place the rear surface 125 on the support surface 124.

After mixing the diluent 66 with the powdered medication 50, the user can position the alignment device 24 so that the rear surface 125 faces generally upward, and partially withdraw the plunger 70 away from the barrel 56 to draw the reconstituted medication into the barrel 56. The user then unlocks the syringe assembly 22 from the alignment device 24 by rotating the barrel handle 80 until the handle flange 90 in the slot 104 is moved out, and then slide the barrel 56 forward to withdraw the needle 58 from engagement with the vial 20 and remove the syringe assembly 22 from the alignment device 24. The user can then administer an injection, and remove the vial 20 from the alignment device 24. The alignment device 24 is then ready for subsequent operation for a next injection.

An embodiment of the alignment device 24 and its method of use discussed above and shown in FIGS. 2–9 has several advantages over conventional devices and methods. For example, the cap receiving surface 118 and overhang 120 allow the user to easily remove the cap 48 from the vial 20. The needle cover engaging surfaces 108, 110 allow the user to easily remove the needle cover 60 from the barrel 56 and needle 58 of the syringe assembly 22. Furthermore, the alignment device 24 allows the user to remove both the cap 48 and the needle cover 60 with the same device which also serves to allow easy alignment of the syringe assembly 22 with the vial.

The alignment device 24 allows users to releasably align the syringe assembly 22 and the vial 20 without getting their hands or fingers in between the needle 58 and the vial 20. Furthermore, the concave vial alignment arms 52 and the syringe alignment arms 98 can more precisely align the vial 20 and the syringe assembly 22, respectively, along the alignment axis 30. Accordingly, the users may be more likely to properly pierce the target area 44 of the vial 20, even in spite of loose manufacturing tolerances in the vial 20 and the syringe assembly 22. Still further, the alignment device 24 can accommodate vials 20 and syringe assemblies 22 having a range of diameters, and can consistently align both the vials 20 and the syringe assemblies 22 on the alignment axis 30 despite the fact that successive vials 20 and/or syringe assemblies 22 may have different diameters. In addition, both the vial 20 and the syringe assembly 22 can be easily removed from the alignment device 24, so that the alignment device 24 is reusable, and can be used repeatedly with different vials and syringe assemblies.

Another advantage is that the syringe assembly 22 can be initially placed on the alignment device 24 from above through the gaps 97 and 99, reducing the likelihood that the needle 58 will come into contact with the alignment device 24. This is unlike conventional devices where the needle 58 approaches the device axially and may strike the device or the hand of the user holding the device. Yet another advantage is that the shape and the contoured surfaces of the barrel handle 80 and the plunger handle portion 76 allow the user to more easily control the motion of these components and therefore reduce the likelihood of contaminating the needle 58 and/or inadvertently puncturing the user's skin with the needle 58.

Figure 4:
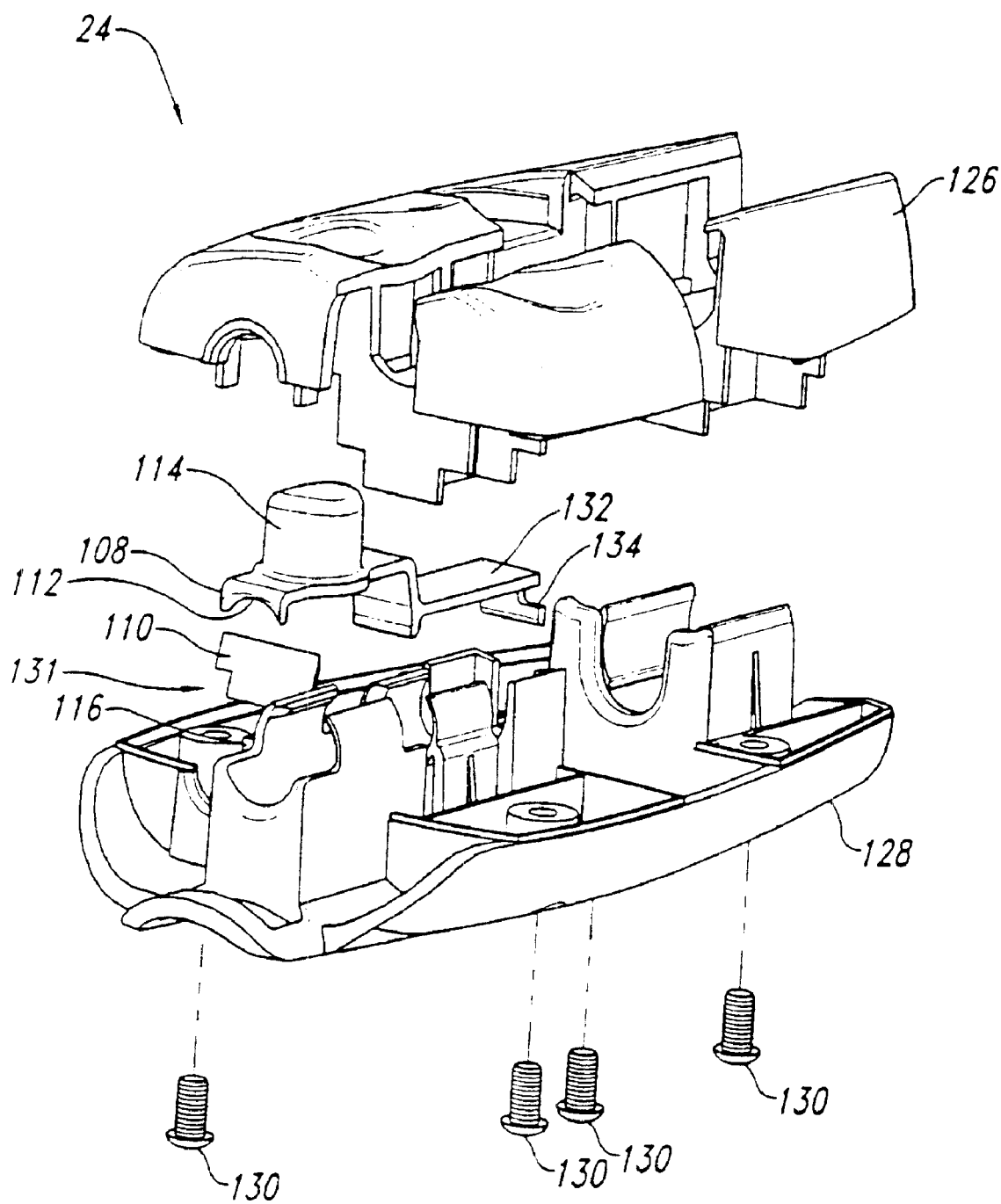
FIG. 4 is an exploded side isometric view of the device shown in FIG. 2.

As shown in FIG. 4, the alignment device 24 can be manufactured from injection molded plastic and can include a molded upper portion 126 and a molded lower portion 128 attached to the upper portion 126 with screws 130. As is also shown in FIG. 4, the lower needle cover engaging surface 110 can include a recessed area 131 that engages a tab (not visible in FIG. 4) to keep the lower needle cover engaging surface 110 in position. Similarly, the upper needle cover engaging surface 108 and the button 114 are attached to a lever 132 that also has a recessed area 134 to engage a corresponding tab (not visible in FIG. 4) to keep the upper needle cover engaging surface 108 in position. The lever 132 is resilient to bias the button 114 upwards.

Figure 6:
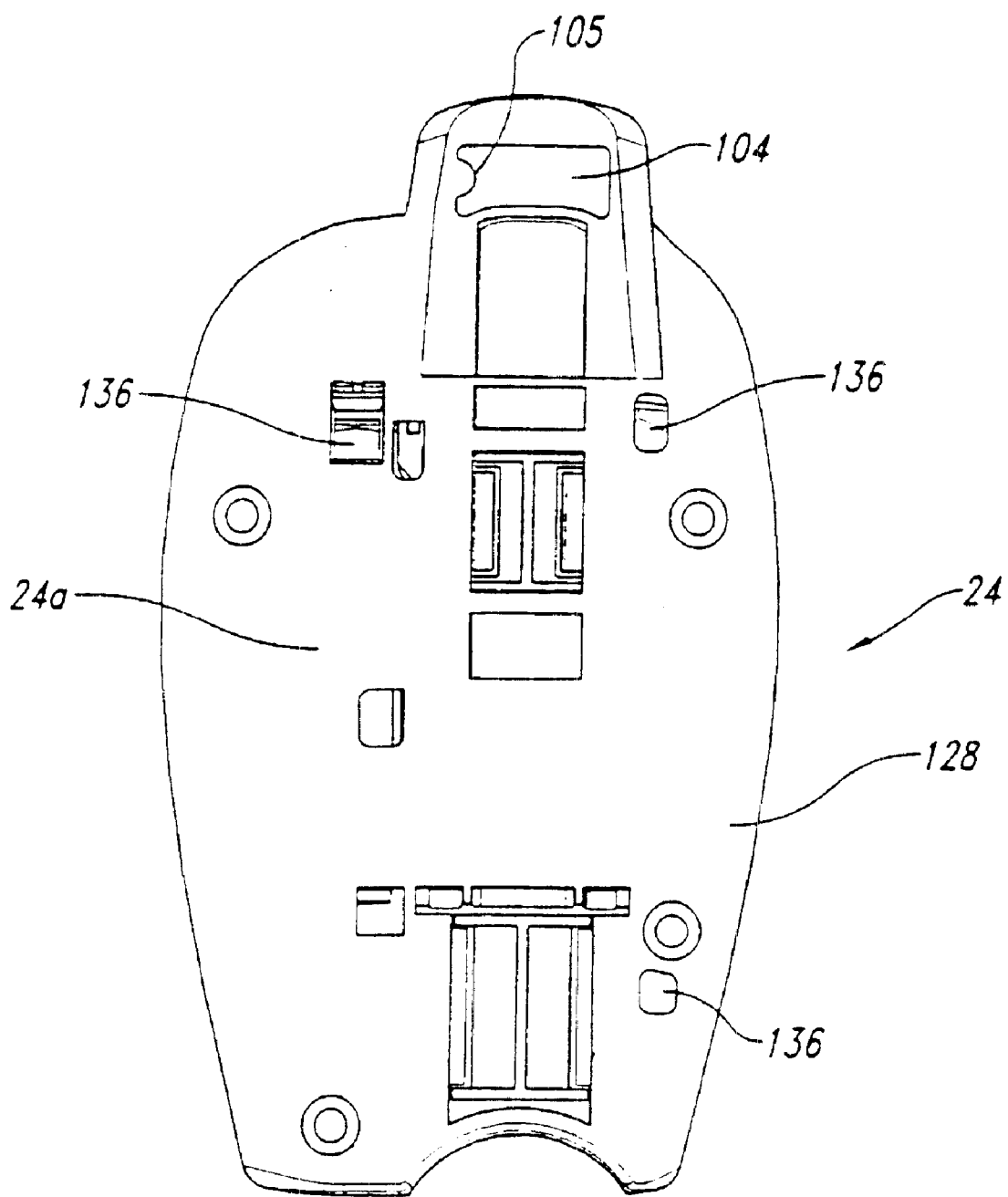
FIG. 6 is a bottom plan view of the device shown in FIG. 2.
Figure 7:
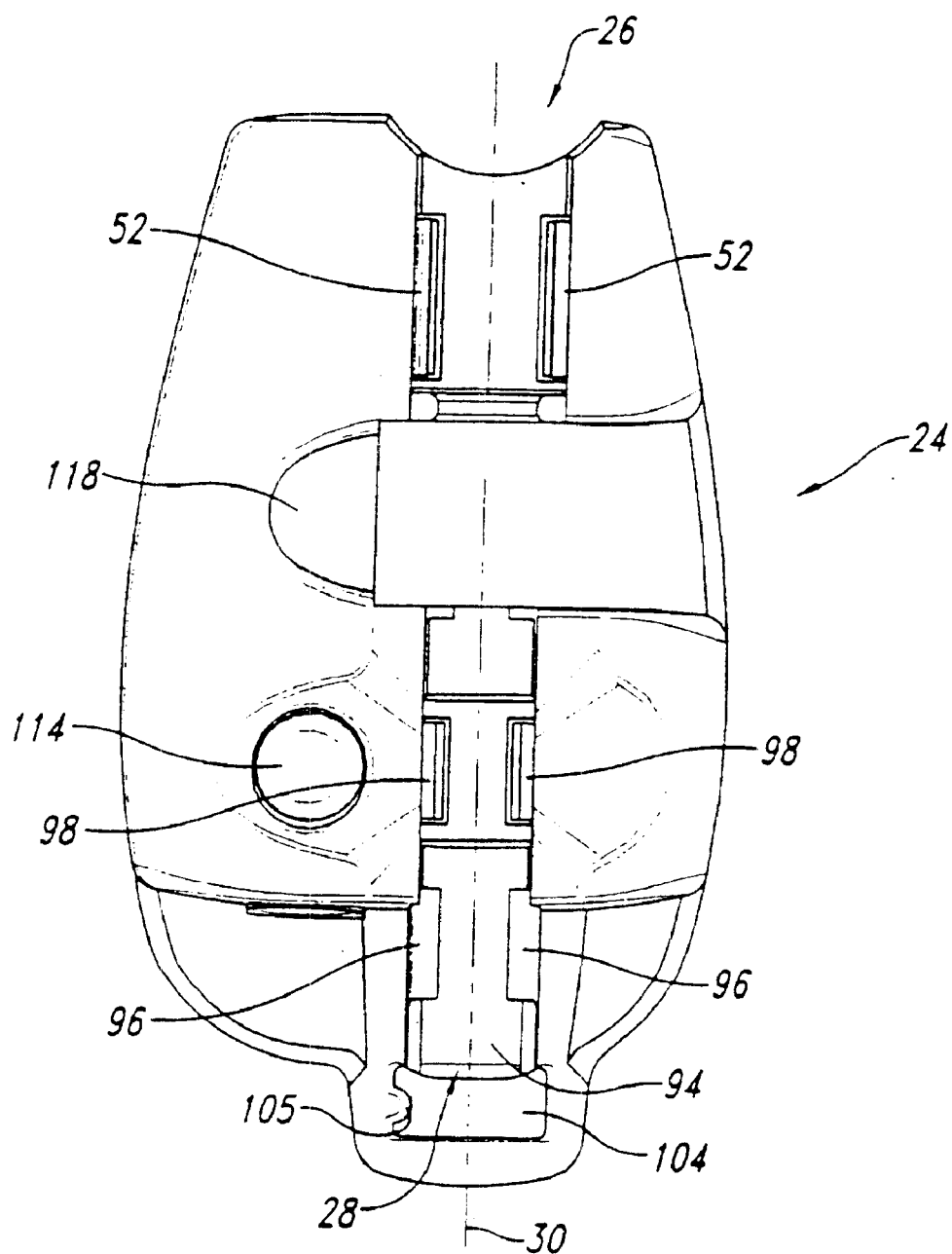
FIG. 7 is a top plan view of the device shown in FIG. 2.
Figure 8:
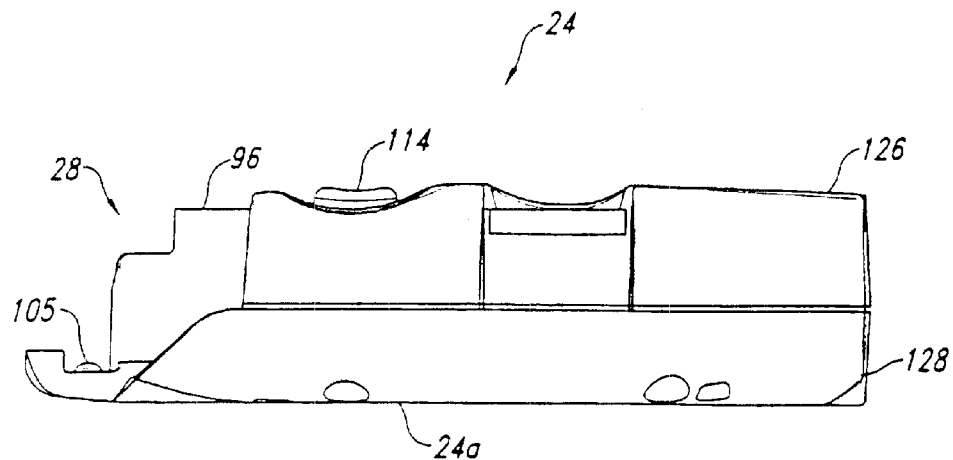
FIG. 8 is a right side view of the device shown in FIG. 2.
Figure 9:
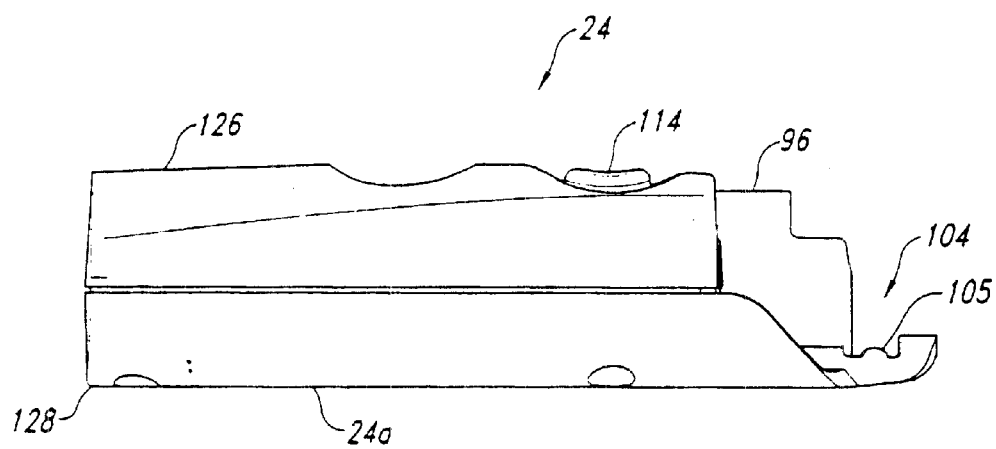
FIG. 9 is a left side view of the device shown in FIG. 2.

As is shown in FIG. 6, the lower portion 128 of the alignment device 24 can include drain apertures 136 that allow any liquids spilled onto or intentionally applied to the alignment device 24 to drain away. For example, the drain apertures 136 can allow water or cleaning solutions to drain away from the alignment device after the device has been immersed for purposes of cleaning.

FIGS. 3, 5, 6, 7, 8, and 9 show the assembled alignment device 24 and more completely display the ornamental external shapes and features of the alignment device 24.

Figure 10A:
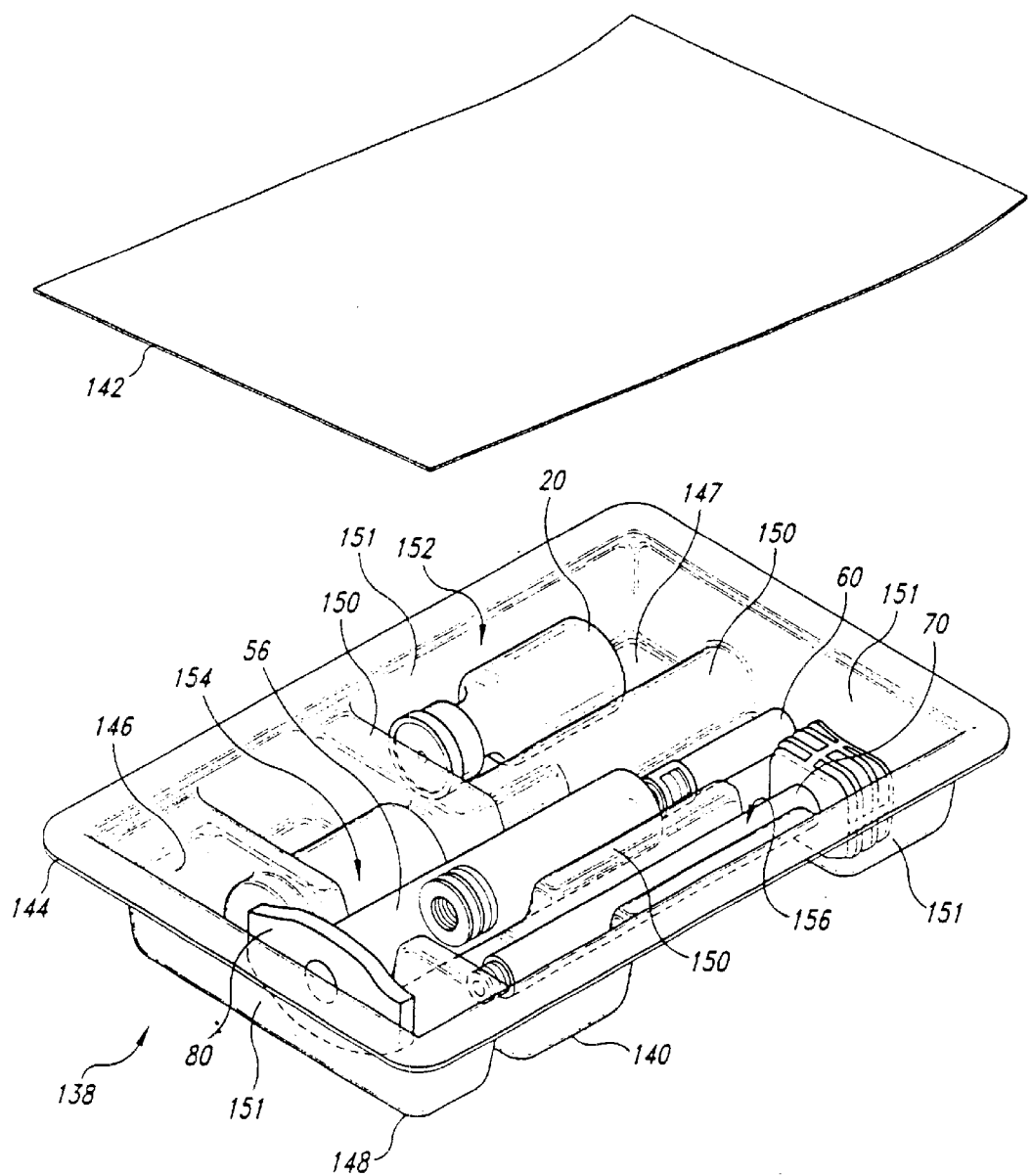
FIG. 10A is a top isometric view of the top side interior of a package for a syringe and a vial in accordance with another embodiment of the invention with a package lid shown removed.

FIG. 10A is a top isometric view of a packaging container 138 for packaging the vial 20 and the syringe assembly 22 shown in FIG. 2. In one embodiment, the container 138 can include a container body 140 having a flexible lid 142 removably attached thereto, but shown removed in FIG. 10A. The container body 140 can include a lip 144 extending around a periphery thereof to which the lid 142 can be adhesively attached.

The container body 140 has an interior surface 146 and an exterior surface 148. The container body 140 can be molded (for example, by thermoforming, vacuum forming or pressure forming) or otherwise formed from a thin walled material such that the interior surface 146 includes a floor 147 having a series of contoured ridges or dividers 150 projecting upwardly therefrom. The dividers 150 and outward perimeter walls 151 are arranged to create separated or partly separated compartments, including a vial receiving area 152 sized and shaped to removably receive the vial 20, a syringe receiving area 154 sized and shaped to removably receive the syringe barrel 56 with the barrel handle 80 and the needle cover 60 attached, and a plunger receiving area 156 sized and shaped to removably receive the plunger 70. Alcohol swabs (not shown) can also be placed in the container body 140.

In a preferred method of operation, the packaging container 138 is positioned so that the exterior surface 148 faces generally downward and the lid 142 faces generally upward. The user peels the lid 142 back to expose the vial 20 and the syringe assembly 22, and removes these articles from the container 138. Once the container 138 has been emptied, the user can invert the container, placing the lip 144 face-down on the flat support surface 124, as is best seen in FIG. 10B, so that the lip 144 stabilizes the container body 140 on the support surface 124.

With the container body 140 face-down on the surface 124, the dividers 150 (which formed receiving areas on the interior surface 146), form a vial alignment portion 26a and a syringe alignment portion 28a on the exterior surface 148 of the container body 140 in coaxial alignment; generally as shown in FIG. 2 of the embodiment first described. As shown in FIG. 10B, the vial alignment portion 26a can include a vial engagement surface 164 having side portions 166 sized to receive and extend at least partially around the vial 20 to restrict both lateral and axial movement of the vial relative to an alignment axis 30a. Similarly, the syringe alignment portion 28a can include a syringe base guide surface 168 and side portions 170 sized to receive and extend at least partially around the barrel 56 of the syringe assembly 22. In a preferred embodiment, the side portions 166 and 170 extend over at least a portion of the upper surfaces of the vial 20 and the barrel 56, respectively, so as to restrict the motion of these components upwardly away from the container body 140. When a sufficiently large upward force is applied to the vial 20, the retaining force of the side portions 160 will be overcome and the vial will release.

The container body 138 can further include a vial stop wall 54a that fits around a portion of the vial neck 36 to restrict axial motion of the vial 20. The container body 138 can also include a syringe stop wall 100a that engages the end face 102 of the syringe barrel 56 to restrict axial motion of the syringe assembly 22.

Figure 10B:
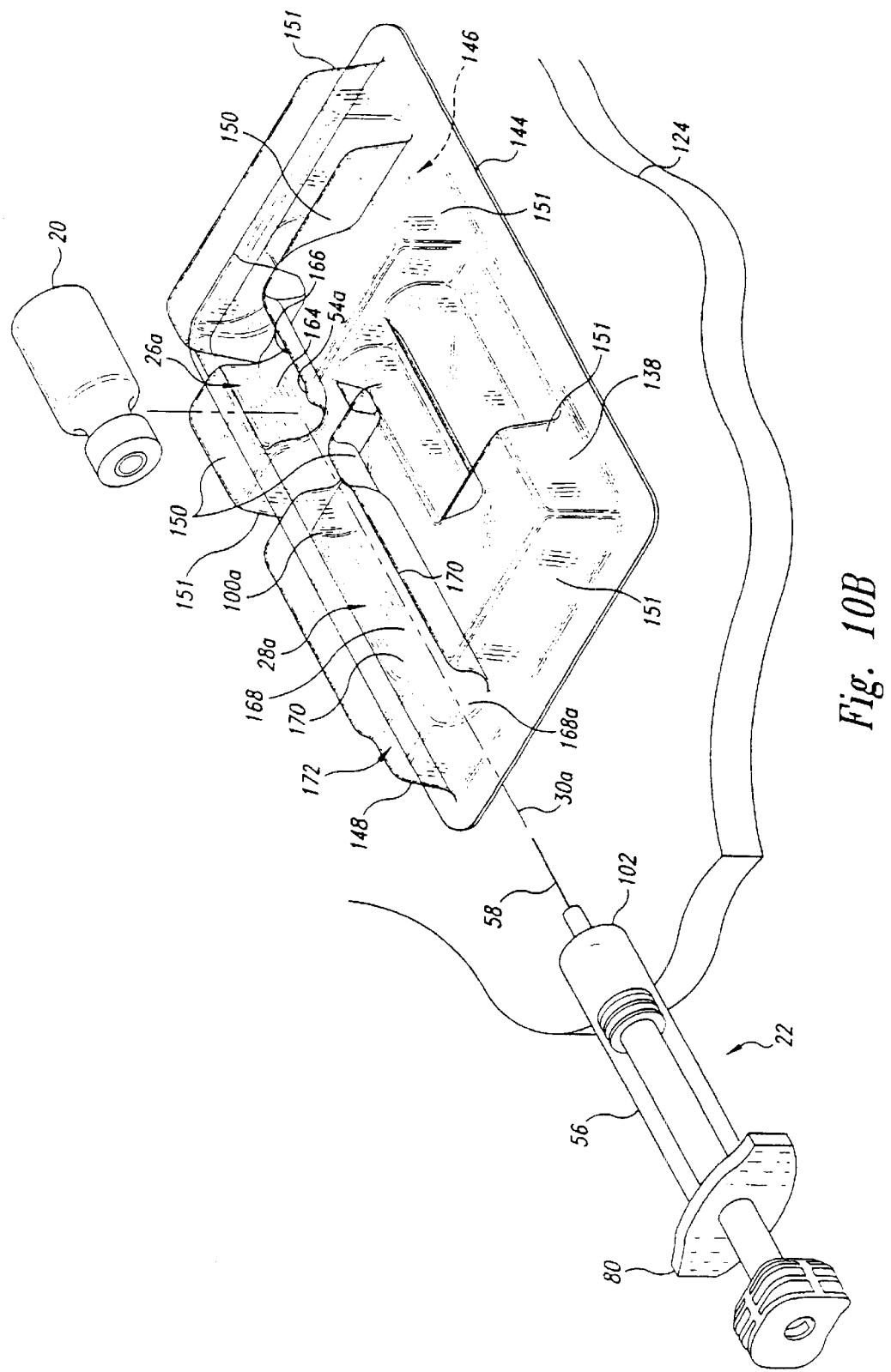
FIG. 10B is a top isometric view of the syringe, the vial and a bottom side surface of the package shown in FIG. 10A.
Figure 10C:
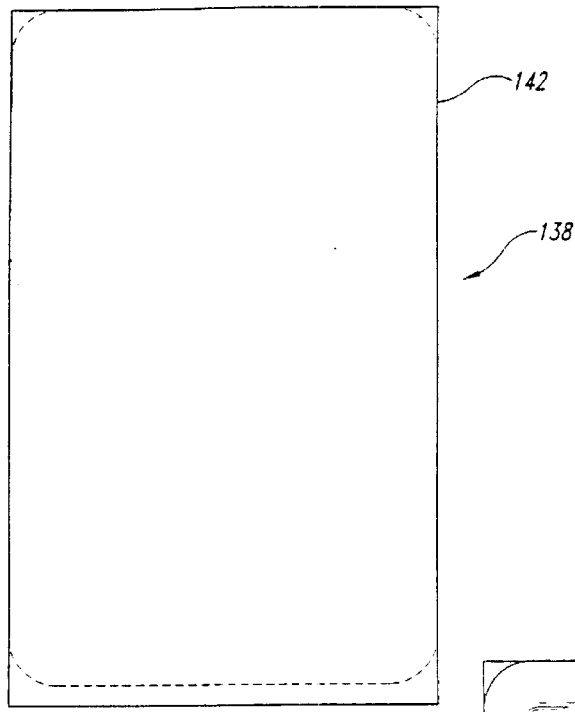
FIG. 10C is a top plan view of the package shown in FIG. 10A with the lid attached.
Figure 10D:
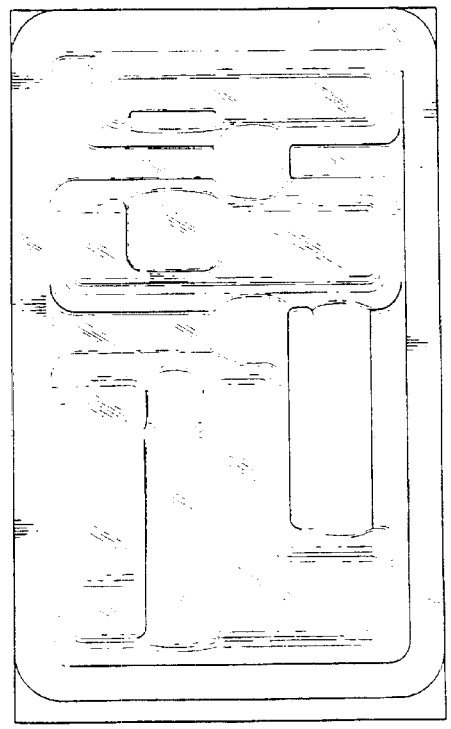
FIG. 10D is a bottom plan view of the package shown in FIG. 10A with the lid attached.
Figure 10E:
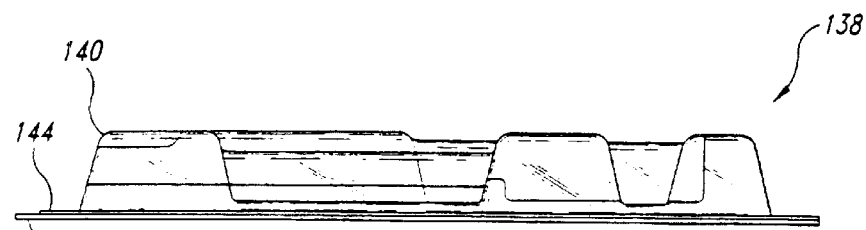
FIG. 10E is a right side elevation view of the package shown in FIG. 10A with the lid attached.
Figure 10F:
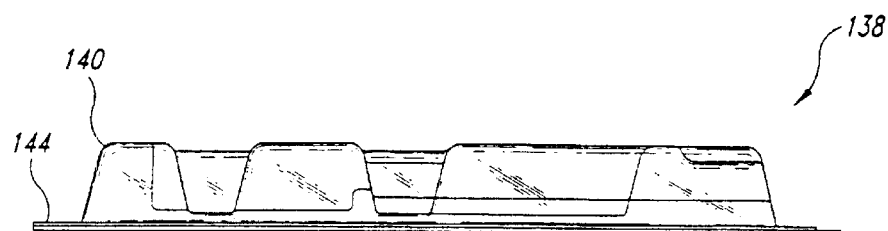
FIG. 10F is a left side elevation view of the package shown in FIG. 10A with the lid attached.
Figure 10G:
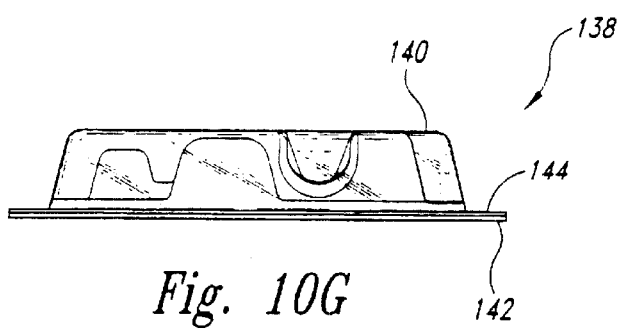
FIG. 10G is a rear elevation view of the package shown in FIG. 10A with the lid attached.
Figure 10H:
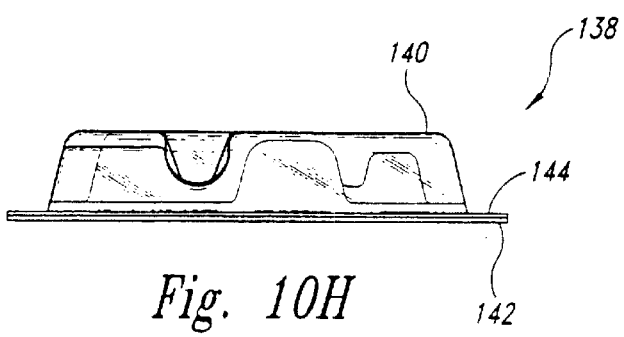
FIG. 10H is a front elevation view of the package shown in FIG. 10A.

As is shown in FIG. 10B, the one side portion 170 of the syringe alignment portion 28a toward a forward end thereof has a reduced height end portion 172. The reduced height portion 172 does not extend laterally outward over the syringe base guide surface 168 as far as the remainder of the side portion 170, thus an enlarged upward, forward end opening is provided to allow unobstructed downward movement of end portion 56a of the barrel 56 to a front end portion 168a of the base guide surface 168. Once the end portion 56a of the barrel 56 is on the front end portion 168a, the barrel can be moved axially along the alignment axis 30a toward the syringe stop wall 100a and the vial 20 in a manner similar to that described above with reference to the base guide surface 94 shown in FIG. 2. Accordingly, the steps performed to align the vial 20 and the syringe assembly 22 using the container 138 are generally similar to the steps discussed above with reference to the alignment device 24 shown in FIG. 2. An advantage of the container 138 is that it serves the dual purpose of containing the syringe assembly 22 and the vial 20 for shipping and storage, and also aligning the syringe assembly and the vial. Accordingly, the user can use the container 138 to align the syringe assembly 22 and the vial 20 when, for example, the alignment device 24 shown in FIG. 2 is not available.

FIGS. 10C–10H show the packaging container 138 and more completely display the ornamental external shapes and textures of the container. In the embodiment shown in FIGS. 10A–10H, the container body 140 is transparent, and in other embodiments, the container body can be translucent or opaque.

From the foregoing it will be appreciated that, although specific embodiments of the invention have been described herein for purposes of illustration, various modifications may be made without deviating from the spirit and scope of the invention. For example, while the devices described above are generally configured to allow the syringe assembly 22 to be moved axially toward the vial 20, in alternate embodiments, the vial 20 can be moved axially toward the syringe assembly 22. Accordingly, the invention is not limited except as by the appended claims.

What is claimed is:

1. A device (24) for aligning a syringe (22) with a vial (20), the device (24) comprising a body (25) having a vial alignment portion (26) and a syringe alignment portion (28) aligned on an alignment axis (30) extending between the vial alignment portion (26) and the syringe alignment portion (28), the vial alignment portion (26) having at least one vial engagement member adapted to engage a vial (20) and align the vial with the alignment axis during operation, the syringe alignment portion (28) adapted to align a syringe (22) with the alignment axis during operation and to limit lateral displacement of the syringe from the alignment axis, the syringe alignment portion including a first guide portion and a second guide portion axially aft of the first guide portion, the first guide portion being upwardly facing, generally aligned with the alignment axis (30), and being substantially located below the alignment axis such that the first guide portion is completely open above the alignment axis, the second guide portion being integral with the first guide portion and having lateral walls extending upward beyond the first guide portion, the lateral walls defining a second opening facing transverse to the alignment axis, the second opening being smaller than the opening in the first guide portion, the first and second guide portions defining an axial sliding surface to accommodate axial sliding of a syringe (22) during use.

2. The device (24) of claim 1 wherein the syringe alignment portion (28) includes a first syringe arm (98) and a second syringe arm (98) spaced apart from the first syringe arm (98), the first and second syringe arms (98) having concave surfaces facing one another, the syringe arms being located on opposite sides of the alignment axis and axially spaced from the second guide portion.

3. The device (24) of claim 1 wherein the first guide portion is concave.

4. The device (24) of claim 1 wherein the body (25) has a cover removing portion that includes first and second cover engaging surfaces (108, 110) spaced apart from one another for claming the cover (60) therebetween.

5. The device (24) of claim 4 wherein at least one of the cover engaging surfaces (108, 110) is movable relative to the other.

6. The device (24) of claim 4 wherein at least one of the cover engaging surfaces (108, 110) includes a sharpened blade.

7. The device (24) of claim 1 wherein the body (25) includes a vial cap removing portion having a generally flat receiving surface (118) adapted to receive an upper surface of a cap (46), the cap removing portion further having an overhanging lip engaging surface (120) located above and spaced apart from the receiving surface (118).

8. The device (24) of claim 2 wherein at least one of the first and second syringe arms (98) is biased toward the other.

9. The device (24) of claim 2 wherein the maximum spacing between the first and second syringe arms (98) is less than the maximum spacing between the lateral arms of the second guide portion.

10. The device (24) of claim 1 wherein the vial engagement member includes first and second vial arms (52) spaced apart from one another on opposite sides of the alignment axis (30), at least one of the first and second vial arms (52) being biased toward the other to releasably clamp a vial (20) therebetween.

11. The device (24) of claim 1 wherein the body (25) includes a slot (104) adapted to receive a flange (90) of a handle (80), and a handle stop (105) positioned in the slot (104) and adapted to prevent rotation of the handle (80) beyond a selected position.

12. The device (24) of claim 1 wherein the syringe alignment portion (28) includes a syringe stop surface (100) adapted to prevent axial translation of a syringe (23) beyond a selected position along the alignment axis (30).

13. A method for aligning a syringe (22) with a vial (20) comprising the steps of:

securing a first vial (20) by removably engaging the first vial (20) with an alignment body (25) to at least restrict motion of the first vial (20) transverse to an alignment axis (30) extending axially from an access port (42) of the first vial (20) when the first vial is secured;

securing a first syringe (22) by laterally moving the first syringe (22) toward the alignment body (25) in a direction transverse to the alignment axis (30), engaging a barrel (56) of the first syringe (22) with a first engagement surface of the alignment body (25) which aligns the first syringe (22) with the alignment axis (30), and axially moving the first syringe (22) along the first engagement surface in general alignment with the alignment axis (30) to engage the syringe (22) with a second engagement surface which limits motion of the first syringe (22) in any direction transverse to the alignment axis (30) such that a needle (58) of the syringe (22) is aligned with and the access port (42) of the vial (20); and reusing the alignment body (25) by removing the first vial (20) and the first syringe (22) therefrom and removably securing a second vial (20) and a second syringe (22) hereto.

14. The method of claim 13 wherein the step of securing the first vial (20) includes restricting motion of the first vial (20) along the alignment axis (30).

15. The method of claim 13 wherein the first syringe (22) includes a barrel (56), a needle (58) projecting from the barrel (56) and a cover (60) adjacent the needle (58) and removably coupled to the syringe, and wherein prior to securing the syringe, the method comprises the steps of clamping the cover (60) between first and second spaced apart cover engaging members (108, 110) of the alignment body (25) and moving the barrel (56) away from the cover

(60) while the cover is clamped between the first and second cover engaging members (108, 110) to separate the cover (60) from the syringe.

16. The method of claim 15 wherein one of the cover engaging surfaces (108, 110) includes a sharpened blade and wherein the step of clamping involves moving the cover (60) into engagement with the sharpened blade.

17. The method of claim 13 wherein the first vial (20) has a removable cap (46), and wherein the method further comprises the steps of:
   engaging the cap (46) with a portion of the alignment body (25); and
   tilting the first vial (20) relative to the alignment body (25) to pry the cap (46) away from the first vial (20).

18. The method of claim 13 wherein the first syringe (22) includes a barrel (56) and a handle (80) attached to the barrel (56), wherein the step of securing the first syringe (22) includes engaging the handle (80) with the alignment body (25).

19. The method of claim 18 wherein the step of engaging the handle with the alignment body includes rotating the handle (80) relative to the barrel (56) about an axis generally parallel with the alignment axis (30) and receiving a flange (90) on the handle in a slot (104) of the alignment body (25).

20. The method of claim 19 wherein the slot (104) includes a handle stop (105), and wherein the step of rotating the handle includes rotating the handle (80) until the handle (80) engages the handle stop (105).

21. A device for aligning a syringe with a vial comprising:
   a body having a vial alignment portion, a syringe alignment portion, and an alignment axis extending between the vial alignment portion and the syringe alignment portion;
   the vial alignment portion having at least one vial engagement surface adapted to align a vial with the alignment axis and to inhibit axial displacement of the vial along the alignment axis; and
   the syringe alignment portion adapted to align a syringe with the alignment axis and to limit lateral displacement of the syringe from the alignment axis, the syringe alignment portion including a guide surface formed on the body and extending along a portion of the alignment axis, the guide surface adapted to slidably guide and support a portion of a syringe, the guide surface having a forward base portion which is substantially located below the alignment axis and open above the alignment axis for laterally receiving a syringe, and two lateral guide surfaces located on opposite sides of the alignment axis aft of the forward base portion, the lateral guide surfaces each including a portion which projects toward the other to define a gap, the gap being located above the alignment axis and having a width that is less than the width of the opening in the forward base portion, the lateral guide surfaces adapted to limit lateral displacement of a syringe.

22. The device of claim 21 wherein the lateral guide surfaces are integrally attached to the base portion such that the combination defined a generally C-shaped channel for receiving a portion of a syringe.

23. The device of claim 21 wherein the syringe alignment portion includes two alignment arms spaced apart from one another on opposite sides of the alignment axis, the alignment arms being located on the body at an axially spaced apart location from the lateral guide surfaces.

24. The device of claim 23 wherein at least one of the first and second alignment arms is biased toward the other.

25. The device of claim 23 wherein the first and second alignment arms are formed integral with the body.

26. The device of claim 21 wherein the vial alignment portion and the syringe alignment portion are formed on one side of the body, and wherein the opposite side of the body includes cavities for storing at least one syringe and at least one vial.

27. The device of claim 21 wherein the vial alignment portion includes a compartment having a lateral width dimension sized to receive a body of a vial, and wherein the at least one vial engagement surface is a vial stop wall located at one end of the compartment, the stop wall having a curved aperture that has a width dimension that is less than the a width of the compartment.

28. The device of claim 21 wherein the at least one vial engagement member includes first and second vial arms spaced apart from one another on opposite sides of the alignment axis, at least one of the first and second vial arms being biased toward the other.

29. The device of claim 28 wherein the first and second vial arms are formed integral with the body.

30. The device of claim 21 wherein the body has a cover removing portion that includes first and second cover engaging surfaces spaced apart to clamp a cover therebetween.

31. The device of claim 30 wherein at least one of the cover engaging surfaces is movable relative to the other.

32. The device of claim 21 wherein the body includes a vial cap removing portion having a generally flat receiving surface adapted to receive the upper surface of the cap, the cap removing portion further having an overhanging lip engaging surface located above and spaced apart from the receiving surface.

33. A device for aligning a syringe with a vial comprising:
   a body having a vial alignment portion, a syringe alignment portion, and an alignment axis extending between the vial alignment portion and the syringe alignment portion;
   the vial alignment portion having at least one vial engagement surface adapted to align a vial with the alignment axis and to inhibit axial displacement of the vial along the alignment axis; and
   the syringe alignment portion adapted to align a syringe with the alignment axis and to limit lateral displacement of the syringe from the alignment axis, the syringe alignment portion including a channel adapted to slidingly guide a syringe along the alignment axis, the channel having a substantially semi-cylindrical shape, the channel having a forward guide portion which is substantially open on one side of the alignment axis, and two lateral guide surfaces extending upward from the channel aft of the forward guide portion, the lateral guide surfaces curving inward toward one another, the lateral guide surfaces having upper edges which define a gap that is less than the side opening in the forward guide portion, the lateral guide surfaces adapted to inhibit lateral displacement of a syringe.

34. A method for aligning a syringe with a vial comprising the steps of:
   providing an alignment body having a vial alignment portion, a syringe alignment portion and an alignment axis extending between the vial alignment portion and the syringe alignment portion;
   securing a vial to the vial alignment portion by removably engaging the vial with the alignment body to limit movement of the vial transverse to an alignment axis; and
   securing a syringe to the syringe alignment portion by laterally moving the syringe toward the alignment body in a direction transverse to the alignment axis to engage a barrel of the syringe with a first guide surface formed on the alignment body which aligns the syringe with the alignment axis, and axially sliding the syringe along the first guide surface in a direction substantially along the alignment axis causing the syringe to engage with a second engagement surface which limits motion of the syringe transverse to the alignment axis, the securing of the syringe placing a needle of the syringe in alignment with an access port of the vial.

* * * * *